(12) United States Patent
Schulz et al.

(10) Patent No.: US 9,975,136 B2
(45) Date of Patent: May 22, 2018

(54) AEROSOL GENERATOR

(75) Inventors: Harald Schulz, Tuttlingen (DE);
Philipp Holzmann, München (DE);
Dominique Mutschmann, München
(DE); Michael Hahn, Krailling (DE)

(73) Assignee: PARI Pharma GmbH, Starnberg (DE)

( * ) Notice: Subject to any disclaimer, the term of this patent is extended or adjusted under 35 U.S.C. 154(b) by 388 days.

(21) Appl. No.: 14/123,634

(22) PCT Filed: Jun. 4, 2012

(86) PCT No.: PCT/EP2012/060488
§ 371 (c)(1),
(2), (4) Date: Apr. 22, 2014

(87) PCT Pub. No.: WO2012/168181
PCT Pub. Date: Dec. 13, 2012

(65) Prior Publication Data
US 2014/0263721 A1    Sep. 18, 2014

(30) Foreign Application Priority Data
Jun. 8, 2011    (EP) .................................... 11169080

(51) Int. Cl.
*B05B 17/00*    (2006.01)
*A61M 11/00*    (2006.01)
*A61M 15/00*    (2006.01)

(52) U.S. Cl.
CPC ....... *B05B 17/0646* (2013.01); *A61M 11/005* (2013.01); *A61M 15/00* (2013.01);
(Continued)

(58) Field of Classification Search
CPC . B05B 17/0638; B05B 17/06; B05B 17/0607; B05B 17/0646
(Continued)

(56) References Cited

U.S. PATENT DOCUMENTS 5,152,456 A * 10/1992 Ross ................. A61M 15/0085
128/200.16
5,586,550 A    12/1996 Ivri et al.
(Continued)

FOREIGN PATENT DOCUMENTS

EP    1293257 A1    3/2003
EP    1468748 A1    10/2004
(Continued)

OTHER PUBLICATIONS

Oliver Humbach, "Mass production of metal microstructure products", Microproduction, Feb. 2008, 2008, pp. 1-3.
(Continued)

*Primary Examiner* — Arthur O Hall
*Assistant Examiner* — Tuongminh Pham
(74) *Attorney, Agent, or Firm* — Wolf, Greenfield & Sacks, P.C.

(57) ABSTRACT

An aerosol generator for generating an aerosol from a fluid, comprising: a vibratable membrane (22) having a first side (24) for being in contact with the fluid and an opposite second side (25), the membrane having a plurality of through holes (26) penetrating the membrane in an extension direction (E) from the first side to the second side, whereby the fluid passes the through holes from the first side to the second side when the membrane is vibrated for generating the aerosol at the second side, each through hole (26) having along its extension direction (E) a smallest diameter (Ds), a larger diameter (DL) that is larger than the smallest diameter and defined by that diameter that is closest to triple, preferably twice said smallest diameter, each through hole having a nozzle portion (32) defined by that continuous portion of the through hole in the extension direction comprising the smallest diameter of the through hole and bordered by the larger diameter of the through hole, character-
(Continued)

ized in that the ratio of the total length of each through hole (26) in the extension direction to the length of a respective one of said nozzle portions (32) in the extension direction is at least (4), preferably at least (4.5) and most preferred equal to or larger than (5).

4 Claims, 6 Drawing Sheets

(52) U.S. Cl.
CPC .... *A61M 15/0015* (2014.02); *A61M 15/0018* (2014.02); *A61M 15/0085* (2013.01)

(58) Field of Classification Search
USPC ................ 239/102.1, 102.2; 128/200.16
See application file for complete search history.

(56) References Cited

U.S. PATENT DOCUMENTS

| | | | |
|---|---|---|---|
| 6,405,934 B1 | 6/2002 | Hess et al. | |
| 6,962,151 B1 | 11/2005 | Knoch et al. | |
| 2001/0013554 A1* | 8/2001 | Borland | B05B 17/0638 |
| | | | 239/1 |
| 2002/0157956 A1* | 10/2002 | Ikeda | B41J 2/1433 |
| | | | 205/75 |

FOREIGN PATENT DOCUMENTS

| | | |
|---|---|---|
| WO | WO 93/10910 A1 | 6/1993 |
| WO | WO 00/29167 A1 | 5/2000 |
| WO | WO 01/18280 A1 | 3/2001 |
| WO | WO 01/032246 A1 | 5/2001 |
| WO | WO 12/092163 A1 | 7/2012 |

OTHER PUBLICATIONS

Matthias Westermann, "New dimensions in electroforming", Microproduction, Feb. 2011, 2011, pp. 26-29.

Third Party Observations dated Aug. 30, 2016 filed in European Application No. 12725433.2.

International Search Report and Written Opinion dated Sep. 5, 2012 in connection with International Application No. PCT/EP2012/060488.

International Preliminary Report on Patentability dated Dec. 27, 2013 in connection with International Application No. PCT/EP2012/060488.

* cited by examiner

AEROSOL GENERATOR

The present invention relates to an aerosol generator and in particular to an aerosol generator having a vibratable membrane with a plurality of through holes comprising a nozzle portion. More particularly the present invention relates to an optimized nozzle portion.

Aerosol generators are mainly used for industrial, laboratorial, and/or medical application, as well as in the field of consumer products but are not limited thereto. Especially the generation of efficient, reproducible and constant aerosol output for greater liquid volumes is currently insufficiently realized. In all applications which require a constant output or dose over the complete aerosol generation cycle (process) and reproducible output during every application an optimized aerosol generator is needed.

Aerosol generators having a vibratable membrane as described above and defined in the preamble of claim 1 are known by WO 93/10910 A1. The through holes defined in the vibratable membrane may be formed by electroforming such as disclosed in WO 01/18280 A1 or by means of a laser source as described for example in WO 00/29167 A1. Other techniques are, however, as well conceivable.

Further, it might turn out in dose finding studies that relatively high amounts of compound need to be delivered to a user. Yet, some liquids (e.g. medical substances or compounds) may not be administered at high concentration for different reasons. High concentration can be related to disadvantageous physico-chemical properties for the nebulization such as high viscosity (Newtonian fluid or non-Newtonian fluid like thixotrope). Further factors may be surface tension, density, kind of a fluid (solution or suspension), solubility or size of particles in the liquid (e.g. micro or nano suspension). A compound might not be solvable in high concentrations or more generally the liquid containing the compound might not be able to carry high concentrations of the compound (i.e. solution, suspension or colloidal drug formulation for an aerosol application and/or inhalation therapy, like liposomes, proteins, anti-bodies, emulsions, surfactants, viral shells and/or two vectors). Thus, in the administration a relatively large volume of fluid, particularly liquid, needs to be emitted in form of the aerosol. The liquid may contain substance or compounds, for example medical liquids, active substances, drugs or further compounds, such as for therapeutic, analytical and/or diagnostic applications. In standard aerosol generators, such as those mentioned in the above documents a relatively large period of time is required for emitting the entire liquid containing the compound in the form of an aerosol.

Such a long period of time, however, is perceived negative and uncomfortable by a user which can lead to a lower acceptance of the application (e.g. medical aerosol therapy, compromised patient compliance, potentially reduced efficacy of the medical aerosol therapy as well as print or fragrance aerosol applications).

Accordingly, the present invention aims to improve the known aerosol generators in this regard and to provide an aerosol generator that enables the emission of even constant large amounts of fluid, particularly liquid in the form of an aerosol in a shorter period of time.

This objective is resolved by an aerosol generator having the features as defined in claim 1. Embodiments of the present invention are defined in the dependent claims.

The present invention is based on the finding that the length of the nozzle portion of the through holes formed in the vibratable membrane has a significant influence on the total output rate (TOR) of the above aerosol generators. In particular, it has been found that the length of the nozzle portion is directly proportional to the total output rate, wherein the shorter the nozzle portion, the higher the TOR and vice versa. In contrast, it has been found that the diameter and the length of the portions upstream of the nozzle portion within the through hole do not have a significant influence on the TOR, if the nozzle portion is sufficiently short and small in diameter as compared to the upstream portion of the through hole. On the other hand, it has as well been found that the length of the nozzle portion as well has an influence on the geometric standard deviation (GSD) of the droplet size distribution. Low GSDs characterize a narrow droplet size distribution (homogeneously sized droplets), which is advantageous for targeting aerosol to the respiratory system. That is, the longer the nozzle portion the lower the GSD. The particle size (preferable below 5 µm) has a GSD in a range of 2.2 to 1.5.

In view of the above findings, the present invention suggests an aerosol generator for generating an aerosol particularly a medical aerosol, from a fluid, preferably a liquid. The aerosol generator comprises a vibratable membrane having a first side for being in contact with the fluid and an opposite second side, from which the droplets emerge. The membrane may be vibrated by means of a piezoelectric actuator or any other suitable means. The membrane has a plurality of through holes penetrating the membrane in an extension direction from the first side to the second side. The through holes may be formed as previously mentioned by a laser source, electroforming or any other suitable process. When the membrane is vibrating, the fluid passes the through holes from the first side to the second side to generate the aerosol at the second side. Each of the through holes has preferably an entrance opening and an exit opening, wherein a nozzle portion preferably extends from the exit opening over a portion of the through holes towards the entrance opening. The nozzle portion is defined by that continuous portion of the through hole in the extension direction comprising a smallest diameter of the through hole and bordered by a larger diameter of the through hole. The larger diameter of the through hole is defined as that diameter that is closest to triple, preferably only twice that smallest diameter. The smallest diameter of the through hole may correspond to the exit opening. Based on the above findings, the aerosol generator of the present invention has through holes in which the ratio of the total length of each through hole in the extension direction to the length of a respective one of said nozzle portions in the extension direction is at least 4, preferably at least 4.5 and most preferred equal to or larger than 5. In this context, at least 75%, more preferably 90%, even more preferably 95% of the through holes need to fulfill the above ratio. Yet, due to manufacturing intolerances some holes may fall outside the range. It has been proven that a ratio below 4, particularly when used in combination with high viscous fluids, high surface tension or fluids having physico-chemical properties which lead to a reduced TOR, may lead to insufficient and reduced nebulization and thus lengthens the nebulization time. Further, it has been found that a ratio of more than 10 will result in so-called bleeding. Bleeding in this context means that fluid passes the membrane from the first side to the second side even when the membrane is not vibrated. Thus, the second side of the membrane is wetted with fluid or liquid being counterproductive for the nebulization process. Preferred upper limits of the ratio are less than 8 and most preferred at about 6.5 or below. Further, it has been found that these ratios provide for an optimum of an increased TOR and a reasonably low GSD. Thus, this configuration enables to achieve shorter application periods and thus comfort for the patient and effectiveness of the medical compound. This is particularly advantageous if medical compounds are used which due to their physico-chemical properties lead to a reduced TOR or in which the concentration of the active compound is limited so that a greater volume of liquid containing the medical compound is to be administered.

According to one embodiment, it is preferred that the nozzle portion terminates flush with the second side. Hence, the length of the nozzle portion may be defined as that portion starting from the second side towards the first side up to and bordered by the diameter that it is closest to triple, preferably twice the smallest diameter. The smallest diameter will in these cases be located at the second side, as is the exit opening.

In any case, it is preferred that the smallest diameter, that is one border of the nozzle portion is located at that end of the nozzle portion in the extension direction adjacent to the second side and that the larger diameter of the through hole being the other border of the nozzle portion is located upstream of the smallest diameter in the direction in which the fluid passes the through holes during operation.

According to one embodiment, it is preferred that the smallest diameter is smaller than 4.5 μm.

In addition, it is preferred that the total length of a through hole in the extension direction is at least 50 μm, preferably at least 70 μm and most preferred at least 90 μm.

The length of the nozzle portion is preferably less than 25 μm, more preferred less than 20 μm and most preferred less than 15 μm.

According to one embodiment, the through holes may be laser-drilled through holes formed in at least two stages, one stage forming the nozzle portion and the remaining stage/-s forming the remainder of the through holes.

Yet, also other manufacturing methods may be used leading to a nozzle portion which is substantially cylindrical or conical with a tolerance of less than +100% of the smallest diameter, preferably less than +50% of the smallest diameter, more preferably less than +30% of the smallest diameter and most preferred less than +15% of the smallest diameter.

Alternatively, the through holes may as well be formed in an electroforming process. In this instant, but also using other manufacturing methods, the through holes may have a first funnel-shaped portion at the first side and a second funnel-shaped portion at the second side with the nozzle portion in-between the first and the second funnel-shaped portions and defined between the exit opening and the larger diameter. In this instance, the total length of the through holes may as well be defined by the distances from the first side to the exit opening (smallest diameter) only.

In addition, it has been found that the TOR may be further increased when increasing the number of through holes provided in the membrane. This may either be achieved by increasing the active perforated surface of the membrane and maintaining the distance of the through holes relative to each other at the same level, or by means of reducing the distance of the through holes relative to each other and maintaining the active area of the membrane. In addition, these measures may as well be combined. From this perspective, it is advantageous that the membrane comprises between 200 and 8,000 through holes, preferably between 1,000 and 6,000, and most preferred between 2,000 and 4,000 of the through holes. Preferably, more than 2,000 through holes are provided. This feature may as well be implemented in an aerosol generator having a nozzle portion different than described herein.

Figure 3:
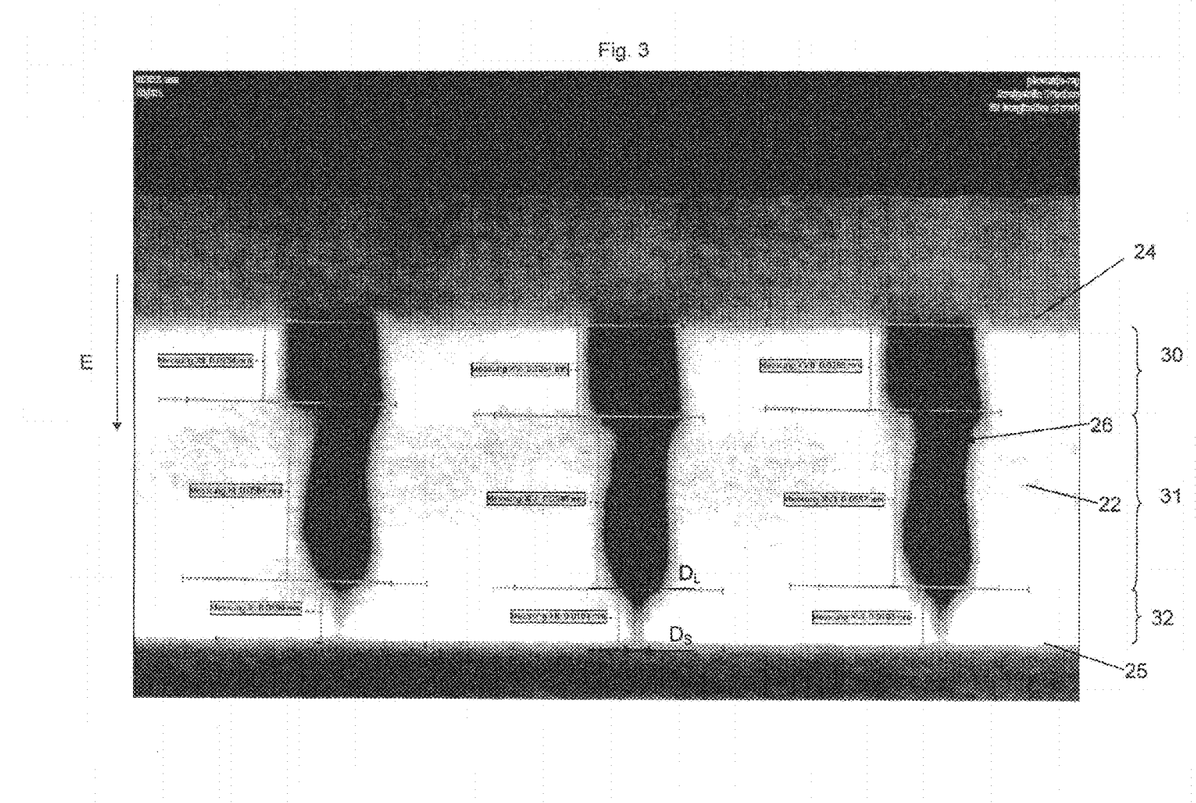

Further adv the total length of the through hole 26 to the length of the corresponding nozzle portion 32 in this embodiment is approximately 5.3.

Figure 4:
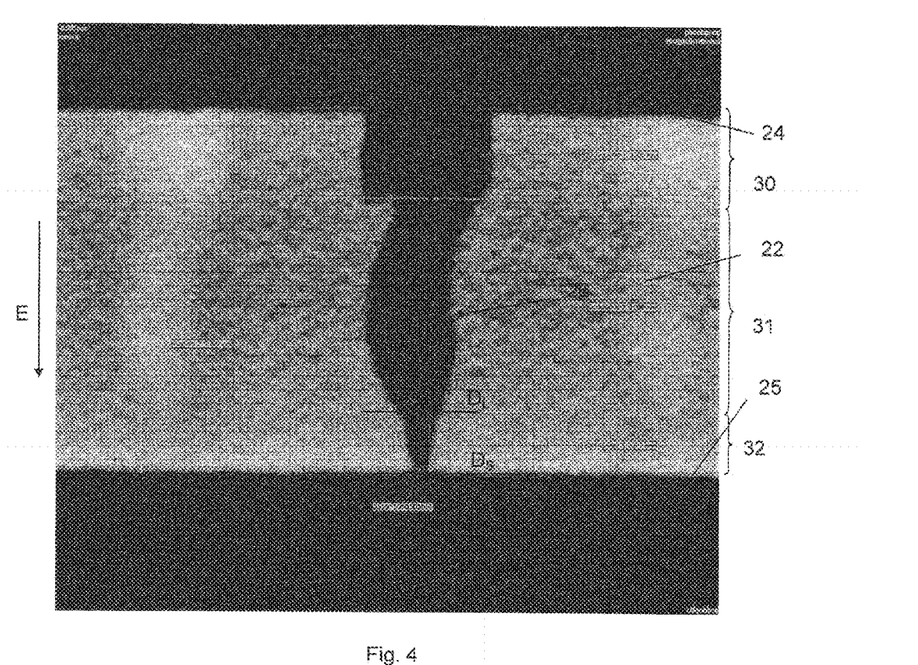

In the embodiment in FIG. 4, however, the first portion 30 has a length of 25 µm, the portion 31 a length of 59 µm and a nozzle portion a length of 17 µm. As a result, the total length of the through hole 26 is 101 µm. Thus, the ratio of the total length of the through hole 26 to the length of the corresponding nozzle portion 32 in this embodiment is approximately 5.9.

Figure 5:
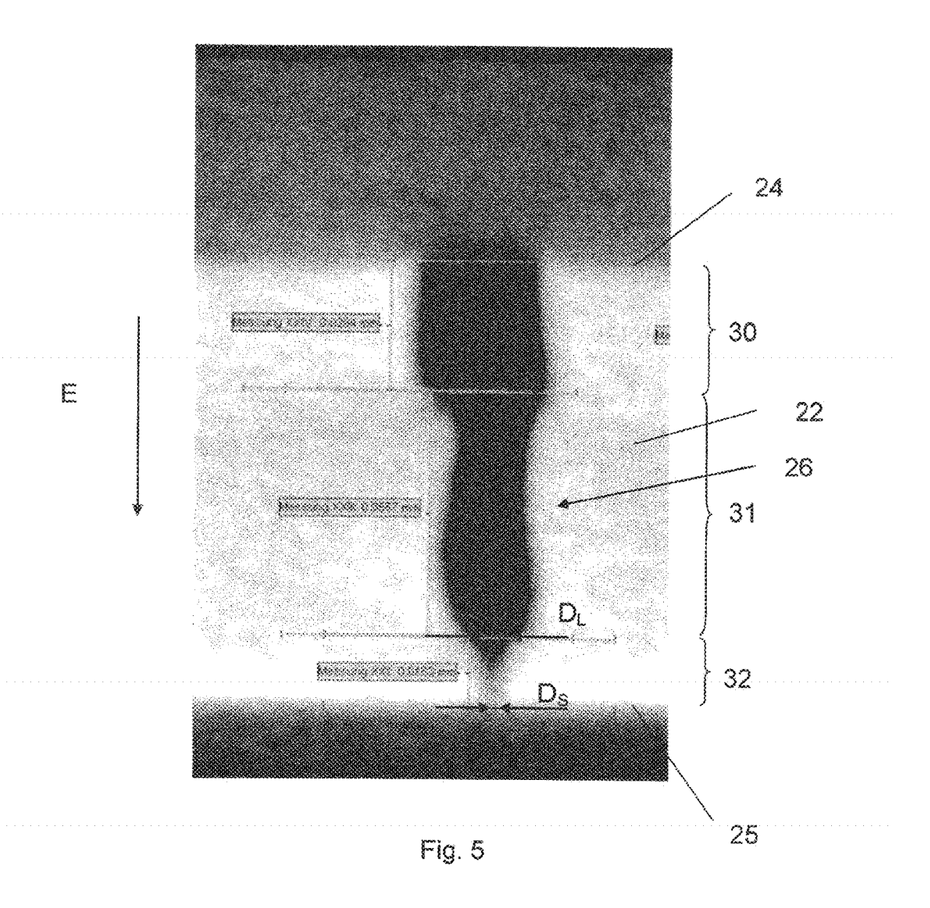

In the embodiment in FIG. 5, however, the first portion 30 has a length of 29.4 µm, the portion 31 a length of 55.7 µm and a nozzle portion a length of 16.3 µm. As a result, the total length of the through hole 26 is 101.4 µm. Thus, the ratio of the total length of the through hole 26 to the length of the corresponding nozzle portion 32 in this embodiment is approximately 6.2.

Figure 6:
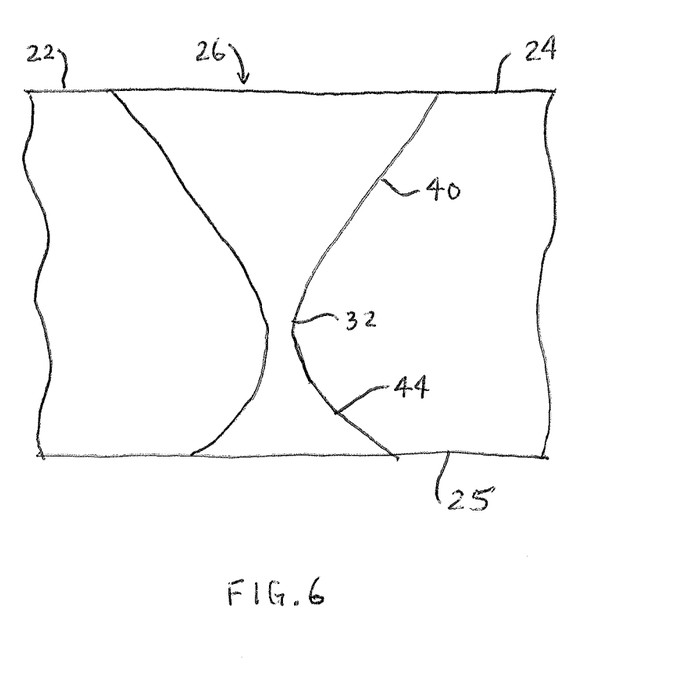

FIG. 6 is a cross-sectional diagram of vibratable membrane 22 having through hole 26. The through hole 26 has a first funnel-shaped portion 40 at the first side 24, a second funnel-shaped portion 44 at the second side 25 and the nozzle portion 32 between the first funnel portion 40 and the second funnel-shaped portion 44.

Figure 1:
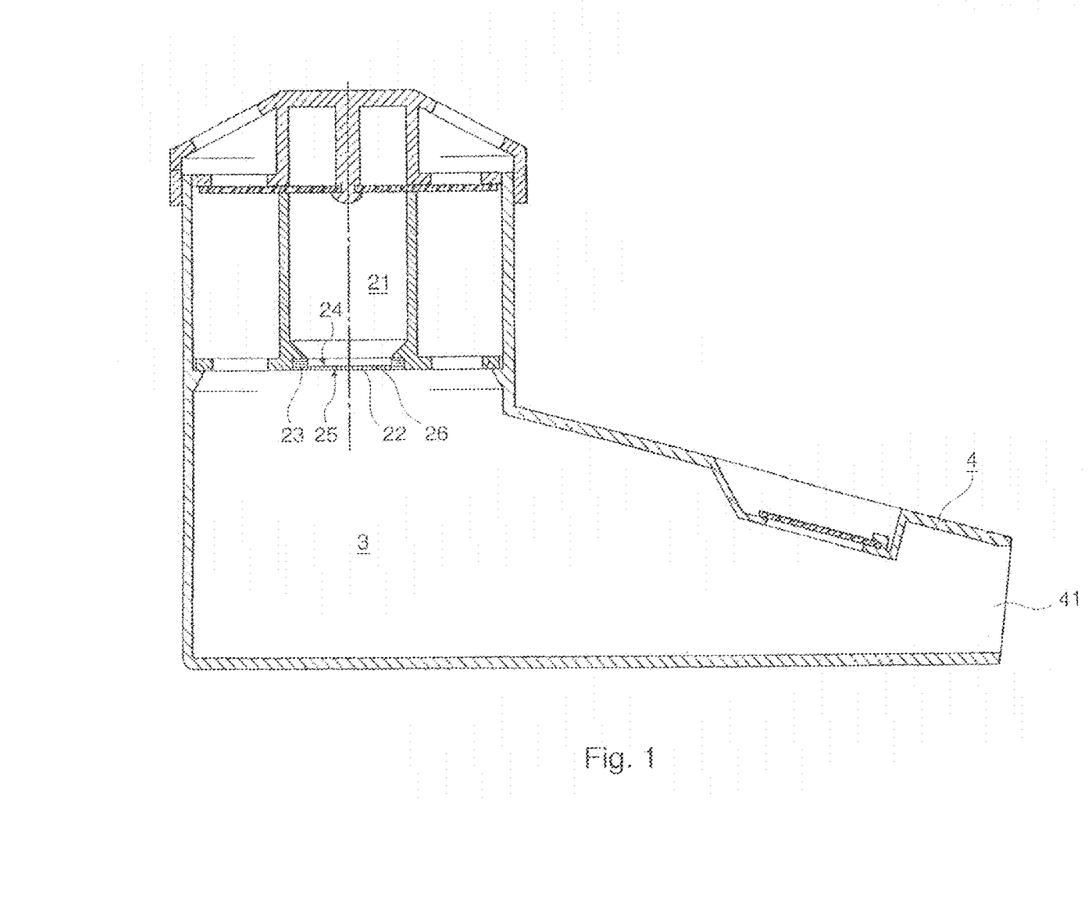
Figure 2:
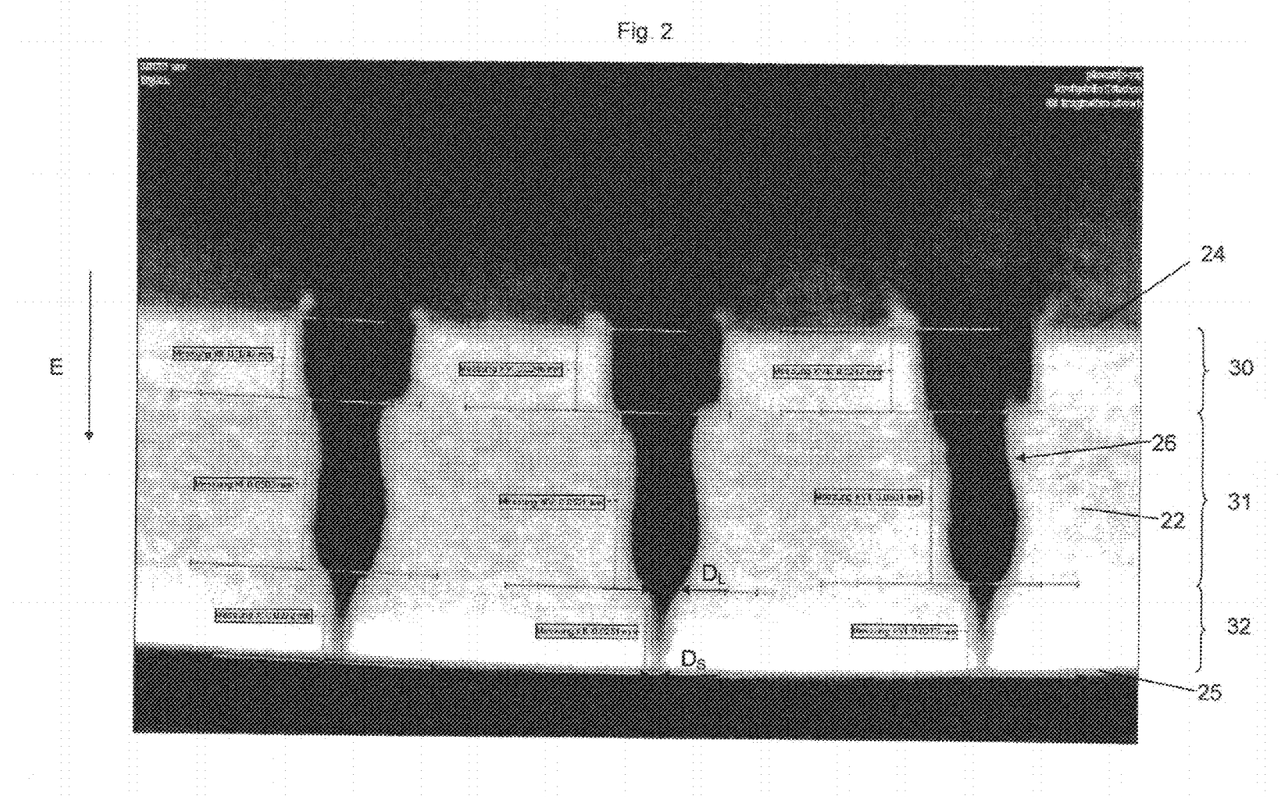

Both the vibratable membranes in FIGS. 2,3 and 5 were manufactured with 6,000 through holes 26. The below table indicates the medium mass diameter (MMD) of the particles emitted at the second side of the membrane, the time required for completely emitting a certain amount of liquid (Neb Time) as well as the TOR. The tests were performed with ARIKACE™, which is a liposomal formulation of amikacine.

TABLE 1

| Membrane | MMD [μm] | Neb time [min] | TOR [g/min] | Number of through holes 26 |
|---|---|---|---|---|
| 1 (shown in FIG. 2 with a nozzle portion of 26 μm) | 4.2 | 14.6 | 0.57 | 6,000 |
| 2 (shown in FIG. 3 with a nozzle portion of 19 μm) | 4.3 | 9.3 | 0.89 | 6,000 |
| 3 (similar to FIG. 3) | 4.4 | 13.4 | 0.62 | 3,000 |
| 4 (similar to FIG. 3) | 4.4 | 11.9 | 0.7 | 3,000 |
| 5 (shown in FIG. 4 with a nozzle portion of 17 μm) | 4.3 | 11.7 | 0.71 | 3,000 |
| 6 (shown in FIG. 5 with a nozzle portion of 16.3 μm) | 4.3 | 9.3 | 0.90 | 6,000 |

The above table shows that the membrane 2 and 6 with the shorter nozzle portion provides for an increased TOR and a reduced nebulization time by 5.3 minutes, that is approximately 36% less as compared to the membrane 1. The above table as well shows that the difference in the MMD is not significant as compared to the significant difference in the TOR. Thus, by means of the present invention, the nebulization time can be reduced significantly, without affecting the droplet size characteristics.

In addition to the membrane shown in FIGS. 2 and 3, membranes were manufactured having the nozzle portion further reduced but with 3,000 through holes 26 only. In particular, a membrane 3 had been laser-drilled with a shorter nozzle portion, whereas a membrane 4 had been manufactured using an even shorter nozzle portion. A further membrane 5 with 3,000 holes is shown in FIG. 4. From the above table, it becomes apparent that even with 3,000 holes (membrane 3,4 and 5) a reduction in the length of the nozzle portion results in an increased TOR compared to membrane 1 with 6,000 holes. The comparison of the membrane 3 and 4 as compared to the membrane 2 further shows that a combination of a higher number of holes (6,000 as compared to 3,000) and a reduced length of the nozzle portion has the strongest effect on increasing the TOR (membrane 2).

Further, it is advantageous to use a laser drilling process as compared to electroforming, as the through holes as shown in FIGS. 2 and 3 are substantially cylindrical or conical as compared to the funnel-shaped entrance and exit of electro-formed through holes as disclosed in WO 01/18280 A1. The vibration of the membrane, that is its vibration velocity, may be transferred to the liquid over a larger area by means of friction when the through holes are substantially cylindrical or conical as compared to the funnel-shaped entrance and exit of electro-formed through holes. The liquid is then because of its own inertia ejected from the exit openings of the through holes resulting in liquid jets collapsing to form the aerosol. Because of the extremely bent surface of the holes of an electro-formed membrane, the surface or area for transferring the energy from the membrane to the liquid is reduced. Yet, the present invention may as well be implemented in electro-formed membranes, wherein the nozzle portion is defined by that continuous portion of the through hole in the extension direction starting from the smallest diameter of the through hole towards the first side until it reaches a diameter triple or preferably only twice said smallest diameter. In this instance, the total length of the through hole is preferably measured from the smallest diameter to the first side.

The present invention of an aerosol generator can be used for different fluids, particularly liquids, for example for applications in the medical, pharmaceutical, diagnostic and/or analytical fields (e.g. human and veterinary aerosol therapies with drugs, substances or active compounds) as well as for agriculture, humidification, fragrance, hairspray, pyrotechnic, warfare agent, combustion engine, extinguishing, lubrication, adhesive, filtering, cooling, painting, printing, varnishing, coating processes, technologies and systems. Further examples are in the field of cell culture, pollen, herbal, medical, chemical, physical, biological, meteorological, pesticide, fungicide, biocide, toxic, environment, and exposition aerosol applications.

Among the active compounds which may be useful for serving one of the purposes named previously and that may be used together with the present invention, are, for example, substances selected from the group consisting of anti-inflammatory compounds, anti-infective agents, antiseptics, prostaglandins, endothelin receptor agonists, phosphodiesterase inhibitors, beta-2-sympathicomimetics, decongestants, vasoconstrictors, anticholinergics, immunomodulators, mucolytics, anti-allergic drugs, antihistaminics, mast-cell stabilizing agents, tumor growth inhibitory agents, wound healing agents, local anaesthetics, antioxidants, oligonucleotides, peptides, proteins, vaccines, vitamins, plant extracts, cholinesterase inhibitors, vasoactive intestinal peptide, serotonin receptor antagonists, and heparins, glucocorticoids, anti-allergic drugs, antioxidants, vitamins, leucotriene antagonists, anti-infective agents, antibiotics, antifungals, antivirals, mucolytics, decongestants, antiseptics, cytostatics, immunomodulators, vaccines, wound healing agents, local anaesthetics, oligonucleotides, xanthin derived agents, peptides, proteins and plant extracts. Such compound may be used in the form of a suspension, a solution, a colloidal formulation (i.e. liposomal), etc.

Examples of potentially useful anti-inflammatory compounds are glucocorticoids and non-steroidal anti-inflammatory agents such as betamethasone, beclomethasone, budesonide, ciclesonide, dexamethasone, desoxymethasone, fluocinolone acetonide, fluocinonide, flunisolide, fluticasone, icomethasone, rofleponide, triamcinolone acetonide, fluocortin butyl, hydrocortisone, hydroxycortisone-17-butyrate, prednicarbate, 6-methylprednisolone aceponate, mometasone furoate, dehydroepiandrosterone-sulfate (DHEAS), elastane, prostaglandin, leukotriene, bradykinin antagonists, non-steroidal anti-inflammatory drugs (NSAIDs), such as ibuprofen including any pharmaceutically acceptable salts, esters, isomers, stereoisomers, diastereomers, epimers, solvates or other hydrates, prodrugs, derivatives, or any other chemical or physical forms of active compounds comprising the respective active moieties.

Examples of anti-infective agents, whose class or therapeutic category is herein understood as comprising compounds which are effective against bacterial, fungal, and viral infections, i.e. encompassing the classes of antimicrobials, antibiotics, antifungals, antiseptics, and antivirals, are

- penicillins, including benzylpenicillins (penicillin-G-sodium, clemizone penicillin, benzathine penicillin G), phenoxypenicillins (penicillin V, propicillin), aminobenzylpenicillins (ampicillin, amoxycillin, bacampicillin), acylaminopenicillins (azlocillin, mezlocillin, piperacillin, apalcillin), carboxypenicillins (carbenicillin, ticarcillin, temocillin), isoxazolyl penicillins (oxacillin, cloxacillin, dicloxacillin, flucloxacillin), and amidine penicillins (mecillinam);
- cephalosporins, including cefazolins (cefazolin, cefazedone); cefuroximes (cefuroxim, cefamandole, cefotiam), cefoxitins (cefoxitin, cefotetan, latamoxef, flomoxef), cefotaximes (cefotaxime, ceftriaxone, ceftizoxime, cefmenoxime), ceftazidimes (ceftazidime, cefpirome, cefepime), cefalexins (cefalexin, cefaclor, cefadroxil, cefradine, loracarbef, cefprozil), and cefiximes (cefixime, cefpodoxim proxetile, cefuroxime axetil, cefetamet pivoxil, cefotiam hexetil), loracarbef, cefepim, clavulanic acid/amoxicillin, Ceftobiprole;
- synergists, including beta-lactamase inhibitors, such as clavulanic acid, sulbactam, and tazobactam;
- carbapenems, including imipenem, cilastin, meropenem, doripenem, tebipenem, ertapenem, ritipenam, and biapenem;
- monobactams, including aztreonam;
- aminoglycosides, such as apramycin, gentamicin, amikacin, isepamicin, arbekacin, tobramycin, netilmicin, spectinomycin, streptomycin, capreomycin, neomycin, paromoycin, and kanamycin;
- macrolides, including erythromycin, clarythromycin, roxithromycin, azithromycin, dithromycin, josamycin, spiramycin and telithromycin;
- gyrase inhibitors or fluroquinolones, including ciprofloxacin, gatifloxacin, norfloxacin, ofloxacin, levofloxacin, perfloxacin, lomefloxacin, fleroxacin, garenoxacin, clinafloxacin, sitafloxacin, prulifloxacin, olamufloxacin, caderofloxacin, gemifloxacin, balofloxacin, trovafloxacin, and moxifloxacin;
- tetracyclins, including tetracyclin, oxytetracyclin, rolitetracyclin, minocyclin, doxycycline, tigecycline and aminocycline;
- glycopeptides, inicuding vancomycin, teicoplanin, ristocetin, avoparcin, oritavancin, ramoplanin, and peptide 4;
- polypeptides, including plectasin, dalbavancin, daptomycin, oritavancin, ramoplanin, dalbavancin, telavancin, bacitracin, tyrothricin, neomycin, kanamycin, mupirocin, paromomycin, polymyxin B and colistin;
- sulfonamides, including sulfadiazine, sulfamethoxazole, sulfalene, co-trimoxazole, co-trimetrol, co-trimoxazine, and co-tetraxazine;
- azoles, including clotrimazole, oxiconazole, miconazole, ketoconazole, itraconazole, fluconazole, metronidazole, tinidazole, bifonazole, ravuconazol, posaconazol, voriconazole, and ornidazole and other antifungals including flucytosin, griseofulvin, tolnaftat, naftifin, terbinafin, amorolfin, ciclopiroxolamin, echinocandins, such as micafungin, caspofungin, anidulafungin;
- nitrofurans, including nitrofurantoin and nitrofuranzone;
- polyenes, including amphotericin B, natamycin, nystatin, flucocytosine; flucytosine
- other antibiotics, including tithromycin, lincomycin, clindamycin, oxazolidinones (linzezolids), ranbezolid, streptogramine A+B, pristinamycin A+B, Virginiamycin A+B, dalfopristin/quinupristin (Synercid), chloramphenicol, ethambutol, pyrazinamid, terizidon, dapson, prothionamid, fosfomycin, fucidinic acid, rifampicin, isoniazid, cycloserine, terizidone, ansamycin, lysostaphin, iclaprim, mirocin B17, cierocidin, filgrastim, and pentamidine;
- antivirals, including aciclovir, ganciclovir, birivudin, valaciclovir, zidovudine, didanosin, thiacytidin, stavudin, lamivudin, zalcitabin, ribavirin, nevirapirin, delaviridin, trifluridin, ritonavir, saquinavir, indinavir, foscarnet, amantadin, podophyllotoxin, vidarabine, tromantadine, and proteinase inhibitors, siRNA-based drugs;
- antiseptics, including acridine derivatives, iodine-povidone, benzoates, rivanol, chlorhexidine, quarternary ammonium compounds, cetrimides, biphenylol, clorofene, and octenidine;
- plant extracts or ingredients, such as plant extracts from chamomile, hamamelis, echinacea, calendula, thymian, papain, pelargonium, pine trees, essential oils, myrtol, pinen, limonen, cineole, thymol, mental, camphor, tannin, alpha-hederin, bisabolol, lycopodin, vitapherole;
- wound healing compounds including dexpantenol, allantoin, vitamins, hyaluronic acid, alpha-antitrypsin, anorganic and organic zinc salts/compounds, salts of bismuth and selen
- interferones (alpha, beta, gamma), tumor necrosis factors, cytokines, interleukines;
- immunmodulators including methotrexat, azathioprine, cyclosporine, tacrolimus, sirolimus, rapamycin, mofetil; mofetil-mycophenolate.
- cytostatics and metastasis inhibitors;
- alkylants, such as nimustine, melphalane, carmustine, lomustine, cyclophosphamide, ifosfamide, trofosfamide, chlorambucil, busulfane, treosulfane, prednimustine, thiotepa;
- antimetabolites, e.g. cytarabine, fluorouracil, methotrexate, mercaptopurine, tioguanine;
- alkaloids, such as vinblastine, vincristine, vindesine;
- antibiotics, such as alcarubicine, bleomycine, dactinomycine, daunorubicine, doxorubicine, epirubicine, idarubicine, mitomycine, plicamycine;
- complexes of transition group elements (e.g. Ti, Zr, V, Nb, Ta, Mo, W, Pt) such as carboplatinum, cis-platinum and metallocene compounds such as titanocendichloride;
- amsacrine, dacarbazine, estramustine, etoposide, beraprost, hydroxycarbamide, mitoxanthrone, procarbazine, temiposide;
- paclitaxel, gefitinib, vandetanib, erlotinib, poly-ADP-ribose-polymerase (PRAP) enzyme inhibitors, banoxantrone, gemcitabine, pemetrexed, bevacizumab, ranibizumab. Examples of potentially useful mucolytics are DNase, P2Y2-agonists (denufosol), drugs affecting chloride and sodium permeation, such as N-(3,5-Diamino-6-chloropyrazine-2-carbony)-N'-{4-[4-(2,3-dihydroxypropoxy)-phenyl]butyl}guanidine methanesulfonate (PARION 552-02), heparinoids, guaifenesin, acetylcysteine, carbocysteine, ambroxol, bromhexine, tyloxapol, lecithins, myrtol, and recombinant surfactant proteins.

Examples of potentially useful vasoconstrictors and decongestants which may be useful to reduce the swelling of the mucosa are phenylephrine, naphazoline, tramazoline, tetryzoline, oxymetazoline, fenoxazoline, xylometazoline, epinephrine, isoprenaline, hexoprenaline, and ephedrine.

Examples of potentially useful local anaesthetic agents include benzocaine, tetracaine, procaine, lidocaine and bupivacaine.

Examples of potentially useful antiallergic agents include the afore-mentioned glucocorticoids, cromolyn sodium, nedocromil, cetrizin, loratidin, montelukast, roflumilast, ziluton, omalizumab, heparinoids and other antihistamins, including azelastine, cetirizin, desloratadin, ebastin, fexofenadin, levocetirizin, loratadin.

Examples of potentially useful anticholinergic agents include ipratropium bromide, tiotropium bromide, oxitropium bromide, glycopyrrolate Examples of potentially useful beta-2-sympathicomimetic agents include salbutamol, fenoterol, formoterol, isoproterenol, metaproterenol, salmeterol, terbutaline, clenbuterol, isoetarine, pirbuterol, procaterol, ritodrine, Examples of xanthin derived agents include theophylline, theobromine, caffeine This list, however, is not exhaustive.

The invention claimed is:

1. An aerosol generator for generating an aerosol from a fluid, comprising:
   a vibratable membrane having a first side for contact with the fluid and an opposite second side, the membrane having a plurality of through holes penetrating the membrane in an extension direction from the first side to the second side, whereby the fluid passes the plurality of through holes from the first side to the second side when the membrane is vibrated for generating the aerosol at the second side, each through hole of the plurality of through holes having along its extension direction a smallest diameter, each through hole of the plurality of through holes having a nozzle portion defined by a continuous portion of a respective through hole of the plurality of through holes along the extension direction from the second side to the first side between the smallest diameter of the respective through hole of the plurality of through holes and a point along the extension direction where the diameter of the respective through hole of the plurality of through holes reaches triple the smallest diameter, wherein
   a ratio of a total length of each through hole of the plurality of through holes in the extension direction to a length of a respective one of said nozzle portions in the extension direction is at least 5 and at most 10, and wherein
   the total length of each of the plurality of through holes in the extension direction is at least 90 µm.

2. The aerosol generator as defined in claim 1, wherein the ratio of the total length of each through hole of the plurality of through holes in the extension direction to the length of a respective one of said nozzle portions in the extension direction is less than 8.

3. The aerosol generator as defined in claim 1, wherein the ratio of the total length of each through hole of the plurality of through holes in the extension direction to the length of a respective one of said nozzle portions in the extension direction is equal to or less than 6.5.

4. The aerosol generator as defined in claim 1, wherein each through hole of the plurality of through holes comprises two portions and the nozzle portion.

* * * * *